United States Patent
Dalio et al.

(10) Patent No.: US 11,651,849 B2
(45) Date of Patent: May 16, 2023

(54) GATHERING AND ANALYZING ASSESSMENT DATA USING CUSTOMIZABLE ONTOLOGIES BUILT UPON A META MODEL

(71) Applicant: PRIOS, LLC, Westport, CT (US)

(72) Inventors: Ray Dalio, Westport, CT (US); David Ferrucci, Wilton, CT (US); Vincent L. Marshall, Wilton, CT (US); Steven Abrams, New City, NY (US)

(73) Assignee: PRIOS, LLC, Westport, CT (US)

( * ) Notice: Subject to any disclaimer, the term of this patent is extended or adjusted under 35 U.S.C. 154(b) by 351 days.

(21) Appl. No.: 16/930,005

(22) Filed: Jul. 15, 2020

(65) Prior Publication Data

US 2021/0020301 A1    Jan. 21, 2021

Related U.S. Application Data

(60) Provisional application No. 62/874,254, filed on Jul. 15, 2019.

(51) Int. Cl.
*G16H 20/70* (2018.01)
*G06Q 10/06* (2012.01)
*G06Q 10/0639* (2023.01)

(52) U.S. Cl.
CPC ....... *G16H 20/70* (2018.01); *G06Q 10/06398* (2013.01)

(58) Field of Classification Search
None
See application file for complete search history.

(56) References Cited

U.S. PATENT DOCUMENTS

| | | | |
|---|---|---|---|
| 2007/0100790 A1 | 5/2007 | Cheyer et al. | |
| 2011/0246530 A1 | 10/2011 | Malafsky | |
| 2012/0143570 A1* | 6/2012 | Austin | G06Q 10/00 703/1 |
| 2013/0205190 A1* | 8/2013 | Kossmann | G06F 16/367 715/225 |
| 2014/0278343 A1 | 9/2014 | Tran | |
| 2015/0199179 A1* | 7/2015 | Gimnich | G06F 8/10 717/104 |

FOREIGN PATENT DOCUMENTS

WO    WO-2016033493 A1 *    3/2016    ....... G06F 17/30294

OTHER PUBLICATIONS

Paulheim et al., "Unsupervised Generation of Data Mining Features from Linked Open Data,"TUD, 2011, 26pg. (Year: 2011).*

(Continued)

*Primary Examiner* — Ryan D. Coyer
(74) *Attorney, Agent, or Firm* — Perkins Coie LLP

(57) ABSTRACT

A meta model may be provided as a global structure providing flexible or customizable options for a specific ontology designed by a system operator. A meta model may include generic structures, such as attributes, attribute categories, and attribute properties. A system operator may configure a set of specific attributes, attribute categories, and synthesis rules within the meta model to define a desired ontology, customizing the system to a specific purpose. A system can receive assertions about points of interest known to the system, and store information about attributes of points of interest based on the specified ontology.

23 Claims, 6 Drawing Sheets

100A

(56) References Cited

OTHER PUBLICATIONS

Rani et al., "Semi-Automatic Terminology Ontology Learning Based on Topic Modeling," Engineering Applications of Artificial Intelligence, 2017, 35pg. (Year: 2017).*
Rinaldi, Antonio M., "An Ontology-Driven Approach for Semantic Information Retrieval on the Web," ACM, 2009, 25pg. (Year: 2009).*
International Search Report and Written Opinion for International Application No. PCT/US2020/042124; dated Oct. 30, 2020; 12 pages.

* cited by examiner

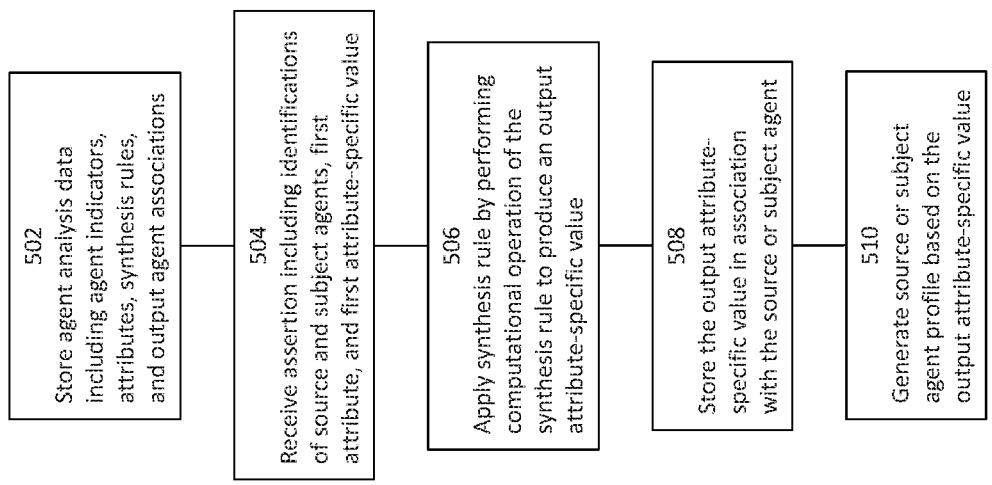

US 11,651,849 B2

GATHERING AND ANALYZING ASSESSMENT DATA USING CUSTOMIZABLE ONTOLOGIES BUILT UPON A META MODEL

CROSS-REFERENCE TO RELATED APPLICATIONS

This application claims priority to U.S. Provisional Application No. 62/874,254 filed Jul. 15, 2019, entitled "GATHERING AND ANALYZING ASSESSMENT DATA USING CUSTOMIZABLE ONTOLOGIES BUILT UPON A META MODEL," the contents of which are incorporated herein in its entirety.

TECHNICAL FIELD

This disclosure generally relates to data management, and in particular, to data collection, aggregation, management, and analysis techniques implementing specific ontologies within a meta model.

BACKGROUND

Defining models of an individual's personal characteristics, which may describe for example how they think, approach problems, related to others, how they are motivated or demotivated, or other characteristics has long been the subject of study in fields like psychology, personality testing, and psychometrics. Different sets of attributes or "Ontologies" have been proposed (e.g., Myers-Briggs Type Indicator, Work Personality Index, the BIG 5). Various testing devices based on scoring answers to a set of questions are used to estimate an individual's vales for the proposed attributes. The results from these tests provide a model of the person or a "picture of what someone is like" according to proposed ontology. That picture can then be used to predict different types of behaviors, or offer information relevant to job performance.

These estimates or models, however, have limited accuracy and limited predictive value. These models only take into account on particular snapshot when the person is tested. They do not take into account development or new data unless the person is subjected to the same test again. The tests predictions are instead assumed to be stable and are infrequently repeated.

Existing computer systems are also not well suited to track a person or group of people within a particular model. For example, quizzes available online simply take in answers to predefined questions and output personality scores based on static rules.

SUMMARY OF THE INVENTION

In some embodiments, a computerized method and system for creating agent profiles is disclosed. In some embodiments, the method and system comprises storing, by a computing device, agent analysis data in a data store, the agent analysis data including: a plurality of agent indicators, a plurality of attributes, and a plurality of synthesis rules, each synthesis rule specifying: at least one associated input attribute of the plurality of attributes, at least one associated output attribute of the plurality of attributes, at least one computational operation to perform on an attribute-specific value associated with the at least one associated input attribute, the computational operation yielding at least one output attribute-specific value for at least one of the at least one associated output attribute, and an output agent association, the output agent association indicating an assignment of the output attribute-specific value to one of a source agent and a subject agent; receiving, by the computing device, an assertion signal from at least one source agent, the assertion signal comprising: an identification of a source agent indicator from the plurality of agent indicators, an identification of a subject agent indicator from the plurality of agent indicators, an identification of a first attribute from the plurality of attributes, and an identification of a first attribute-specific value; applying a synthesis rule of the plurality of synthesis rules based on at least one of: the identification of the source agent indicator, the identification of the subject agent indicator, the identification of the first attribute, and the identification of the first attribute specific value, wherein applying the synthesis rule includes performing the at least one computational operation associated with the synthesis rule to yield the at least one output attribute-specific value; storing the at least one output attribute-specific value in association with at least one of the source agent and the subject agent based on the output agent association of the at least one synthesis rule; and generating at least one of a source agent profile and a subject agent profile based on the stored at least one output attribute-specific value.

In some embodiments, the plurality of attributes are configurable based on a specified ontology.

In some embodiments, the performing the at least one computational operation is based on one of the identification of the source agent indicator and the identification of the subject agent indicator, and wherein the performing the at least one computational operation comprises retrieving at least one of: at least one first stored attribute-specific value for the first attribute stored in association with the one of the identification of the source agent indicator and the identification of the subject agent indicator; and at least one second stored attribute-specific value for a second attribute different from the first attribute stored in association with the one of the identification of the source agent indicator and the identification of the subject agent indicator.

In some embodiments, the computational operation further comprises at least one of: comparing the at least one first stored attribute-specific value or the at least one second stored attribute-specific value to a threshold; and comparing at least one first stored attribute-specific value or the at least one second stored attribute-specific value to the first attribute-specific value from the assertion signal.

In some embodiments, the computational operation comprises at least one of: averaging attribute values associated with the subject agent indicator; filtering attribute values associated with the subject agent indicator based on a threshold; weighting attribute values associated with the subject agent based on stored information associated with at least one of the subject agent indicator and the source agent indicator; computing an update to the stored first attribute-specific value associated with at least one of the source agent indicator and the subject agent indicator; computing an update to the stored second attribute-specific value associated with at least one of the source agent indicator and the subject agent indicator.

In some embodiments, the stored information comprises a believability score associated with at least one of the subject agent indicator and the source agent indicator.

In some embodiments, the generating at least one of a source agent profile and a subject agent profile based on the output attribute-specific value comprises generating text summarizing at least the output attribute-specific value and at least one other assertion.

In some embodiments, the identified subject agent indicator represents a person, and at least one of the plurality of attributes comprises an observable attribute of at least one of a person's personality or cognitive style.

In some embodiments, the receiving, by the computing device, an assertion signal from the at least one source agent comprises receiving a plurality of assertion signals to yield a plurality of output attribute-specific values for at least one subject agent.

In some embodiments, the computerized method comprises adjusting at least one of the plurality of output attribute-specific values based on others of the plurality of output attribute-specific values.

In some embodiments, the adjusting the at least one of the plurality of output attribute-specific values comprises normalizing the plurality of output attribute-specific values to an expected or desired distribution.

In some embodiments, the computerized method comprises: comparing at least one of the plurality of output attribute-specific values associated with one subject agent and one attribute with at least one of a threshold and others of the plurality of output attribute-specific values associated with the one attribute; and identifying if the at least one of the plurality of output attribute-specific values is an outlier.

In some embodiments, the computerized method comprises: ranking at least two subject agents based on output attribute-specific values associated with the at least two subject agents for at least one attribute.

In some embodiments, the computerized method comprises: generating a second assertion signal associated with at least one of the two subject agents based on the ranking.

In some embodiments, the computerized method comprises: generating a graphical user interface to provide a user with access to at least a subset of the plurality of output attribute-specific values, wherein the graphical user interface includes: at least one selection input configured to select output attribute-specific values based on at least one of an agent indicator, an attribute, a specified time period, and a specified attribute-specific value range; and a display element configured to display the at least a subset of the plurality of output attribute-specific values based on input from the at least one selection input.

In some embodiments, the computerized method comprises: updating at least one of the synthesis rules based on the plurality of output attribute-specific values.

In some embodiments, at least one of the identification of the first attribute from the plurality of attributes and the identification of the first attribute-specific value comprises text, audio, or video data, and wherein the computerized method further comprises processing the text, audio, or video data to determine the at least one of the first attribute and the first attribute-specific value.

In some embodiments, the computerized method comprises: associating the assertion signal with at least one event or time.

In some embodiments, the computerized method comprises: comparing the at least one output attribute-specific value with at least one previously generated output attribute-specific value associated with the same attribute to produce an assertion about the at least one event.

In some embodiments, the computerized method comprises: receiving at least one assertion from a non-agent about the subject agent, the assertion comprising: an identification of the subject agent indicator from the plurality of agent indicators, and an identification of the first attribute from the plurality of attributes, and an identification of a non-agent rated first attribute-specific value; storing the non-agent rated attribute-specific value in association with the subject agent; and generating the subject agent profile based on the stored at least one output attribute-specific value and the stored non-agent rated first attribute-specific value.

In some embodiments, the assertion signal comprises one or more of audio, video, and text data, and wherein the identification of the first attribute from the plurality of attributes and the identification of a first attribute-specific value are extracted from the assertion signal using natural language processing.

In some embodiments, the computerized method comprises: generating natural language based on at least one attribute-specific grammatical element and one or more of the at least one output attribute-specific value and the first attribute-specific value.

These and other capabilities of the disclosed subject matter will be more fully understood after a review of the following figures, detailed description, and claims. It is to be understood that the phraseology and terminology employed herein are for the purpose of description and should not be regarded as limiting.

BRIEF DESCRIPTION OF THE DRAWINGS

For a more complete understanding of various embodiments of the disclosed subject matter, reference is now made to the following descriptions taken in connection with the accompanying drawings, in which:

FIG. 5 is a flowchart illustrating a method of creating agent profiles, according to some embodiments of the present disclosure.

DETAILED DESCRIPTION

Figure 1A:
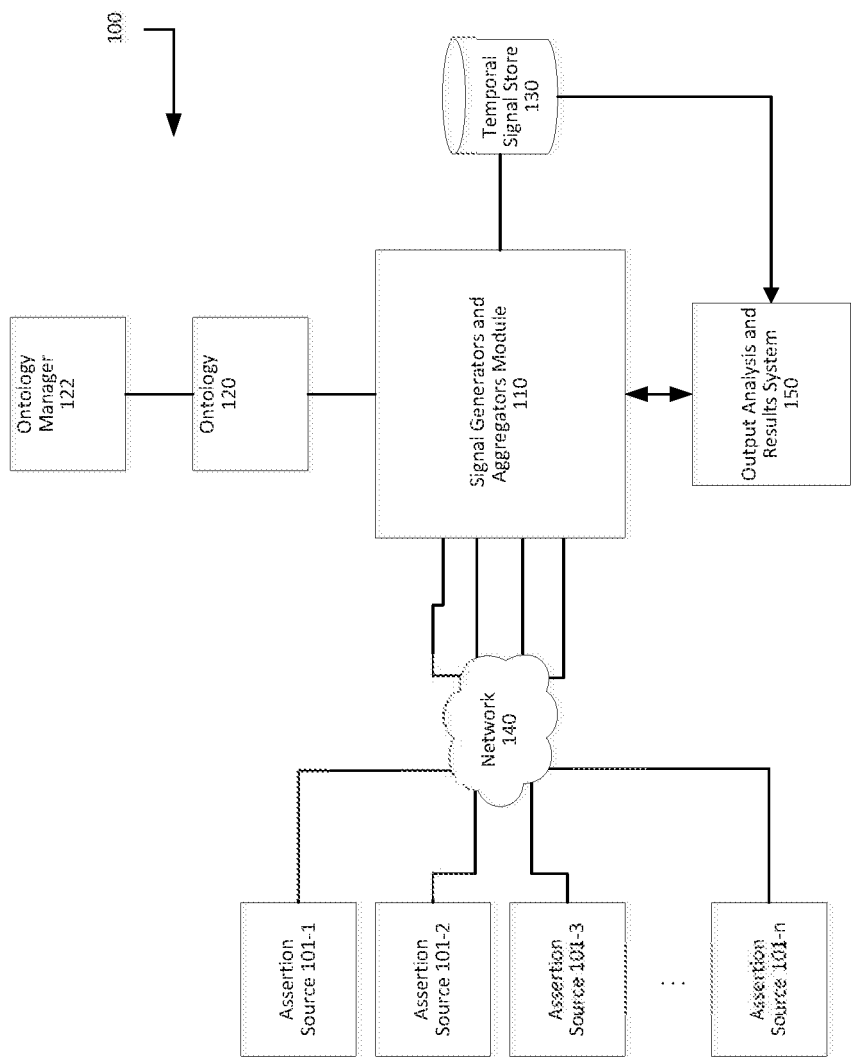
FIGS. 1A-1B illustrate exemplary systems for implementing ontologies, according to some embodiments of the present disclosure.

Some embodiments described herein relate to a meta model that defines a base language for expressing information. The meta model defines certain types or classes of things upon which an ontology can be built to develop information about points of interest.

According to an embodiment, a meta model may be provided as a global structure providing flexible or customizable options for a specific ontology designed by a system operator. A meta model may include generic structures, such as attributes, attribute categories, and attribute properties. A system operator may configure a set of specific attributes, attribute categories, and synthesis rules within the meta model to define a desired ontology, customizing the system to a specific purpose. In other words, the ontology may specify the particular vocabulary that is used to customize the system to a particular purpose. According to some embodiments, this computational structure allows for a system to receive various types of assertions about a point of interest and produce assertions about that point of interest based on the input data.

In some embodiments, an attribute is a characteristic of a point of interest, such as an agent, that can be tracked based on various types of input data. According to the meta model, attributes may be assigned attribute values. Attribute values may be selected from a variety of attribute value types such as, but not limited to a numeric score, a percentage, a binary indication, a ranking relative to other points of interest, a selection of at least one option (e.g., low, medium, or high), or other values. Attribute values may accept or include more than one attribute value type and may be aggregated to produce an aggregated attribute value. According to an embodiment, the point of interest may be a person, item, organization or other physical or conceptual grouping or element about which data is sought.

The meta model can specify that attributes values can be determined based on a variety of types of assertion sources. Signal generators receive the assertions from an assertion source and output signals that are used to alter or confirm attribute values based on synthesis rules. According to some embodiments, signal generators are specific types of synthesis rules that are associated with assertion sources. Other types of synthesis rules are contemplated and discussed throughout the present disclosure. Assertion sources may include, but are not limited to, polls, surveys, tests, text recognition devices or text files, ratings or rankings input by a user of the system (such as an agent) or the system operator, assertions such as an output from a sensor or detector, recorded audio or video signals, biometric assertions, speech pattern recognition algorithms, or other types of assertion sources. Assertion sources may be associated with more than one attribute, and each attribute may be associated with more than one assertion source. However, the ontology is independent of the types or formats of assertion sources. The ontology may define in which ways certain signals from assertion sources may alter attribute values. Attribute values may also be associated with attribute confidences which indicate a level of confidence for the attribute value based on the collected assertions. Attribute value confidences may be developed from the sources themselves or input manually by a system operator.

The meta model can specify that attributes can be grouped into attribute categories. Attribute categories can be used to organize attributes into groupings with similar characteristics. By nesting particular attributes under broader attribute categories, a system may use an assertion about an attribute to compute an assertion (or the likelihood of an assertion) about another attribute within the same category, or about the category itself.

The meta model specifies that one or more synthesis rules can operate on assertions received or generated by the system. Synthesis rules allow for assertions, such as an assertion about an attribute of an agent, to trigger the computation of additional assertions or refinement of the original assertion. For example, a synthesis rule may take the form of an attribute property. For example, an attribute may be a "takes-one-to-know-one" attribute. The "takes-one-to-know-one" property takes advantage of the fact that synthesis rules may act in a way dependent upon the attributes of an agent and the attributes of an attribute. For a "takes-one-to-know-one" attribute, an assertion from a source agent about a subject agent regarding a "takes-one-to-know-one" is prioritized based on whether the source agent does or does not possess the "takes-one-to-know-one" attribute. This may be based on a binary determination, a threshold, or other type of value-driven weighting. Whether or not a particular attribute is a "takes-on-to-know-one" attribute is part of a specific ontology.

According to an embodiment, another synthesis rule may include interrelations between attributes. For example, changing the value of a first attribute may affect the value of a second attribute depending on the interrelation between the first and second attributes. A particular synthesis rule may select amongst a variety of types of interrelations included in the meta model, and more particularly by particular elements specified by the ontology within the meta model. These may take the form of attribute/sub-attribute, for example, where an attribute category is an attribute itself. Synthesis rules that are based on attribute interrelations may be more complex and are discussed in more detail below.

According to an embodiment, another attribute property may be a linguistic association. For example, the meta model may allow synthesis rules to specify particular associations between points of interest having certain attribute values and certain linguistic terms or phrases. Words or phrases may be positively or negatively associated with an attribute. For example, for an attribute such as "humility," the term "overconfident" may be negatively associated whereas the term "humble" may be positively associated.

According to an embodiment, synthesis rules may take the form of action associations. For example, the meta model may allow synthesis rules to specify particular associations between agents having certain attribute values and certain actions. Action associations may work in both directions. For example, an action association may involve receiving an indication that an agent took a certain action and relate the simple performance of that action (or quality of performance of that action) and making an assertion based on that action. For example, when an employee is frequently at the office after hours, it may be determined that the employee is a hard worker. Action associations may work in the other direction as well. For example, if an agent has been determined to have strong leadership skills, it may be possible to predict a certain action in the future, for example that the agent will take charge for a new project. Various implementations may use these predictive assertions to either indicate propensity for particular actions or as a threshold to permit agents to take certain actions (e.g., only those with leadership attributes may be promoted to managers).

According to some embodiments, assertions may be associated with particular events or settings. For example, an assertion may be made about one agent by another at a meeting in the workplace. Synthesis rules may be event-specific. Accordingly, certain synthesis rules may be applied based on assertions received at particular events (e.g., meetings).

According to an embodiment, the ontology may be customized at an intermediate level of generality for a particular application or field. For example, as discussed in more detail below, the ontology may be configured for management of persons within an institution or group. Attribute values may be determined and tracked for each person, such as employees, within the institution or group. These attribute values may be used to make decisions, and may further be used to optimize hiring decisions or institutional structure, such as promotions. A given institution or group may select an ontology of attributes, attribute categories, and attribute properties that suits that institution's particular needs.

According to an embodiment, attribute values may be tracked over time. Tracking attribute values over time may include storing each signal used to determine attribute values. Accordingly, when new signals are received, attribute values may be updated based on existing and new signals. These signals, in aggregate, may be used to take certain actions, such as select a desired attribute set or range for a desired point of interest. The signals may also be assigned a timestamp, for example, for weighting attribute values as discussed in more detail in this disclosure.

A system operator may define an ontology within the meta model. Defining the ontology may involve defining particular attributes, attribute categories, attribute relations, and assertion sources. According to an embodiment, the ontology may be defined based on a range of preset ontology elements, such as predefined attributes, attribute categories, synthesis rules, and assertion sources. According to another embodiment, the ontology may be set as a default, and may be adjusted or expanded by the system operator.

FIG. 1A illustrates an exemplary system 100 for generating assertions, according to some embodiments of the present disclosure. System 100 includes assertion sources 101-1 through 101-n, signal generators and aggregators module (SGAM) 110, ontology 120, ontology manager 122, temporal signal store 130, network 140, and output analysis and results system-150.

The ontology manager 122 can be used by a system operator to selectively configure an input ontology 120 using the language of a meta model. As described in more detail below, inputs to the ontology manager 122 can be mapped or translated into an input ontology 120, which can include ontology items such as attributes, attributes categories, synthesis rules, and assertion sources. The input ontology 120 can then be provided to the signal generators and aggregators module (SGAM) 110.

Assertion sources 101-1 through 101-n collect assertions relating to and/or originating from at least one point of interest, such as an agent. Assertion sources 101-1 through 101-n provide an assertion, e.g. via the network 140, to the SGAM 110. As described above, assertion sources can include polls, surveys, tests, text recognition devices or text files, ratings or rankings input by a user of the system or the system operator, data such as that output from a sensor or detector, and recorded audio or video signals.

The SGAM 110 aggregates the assertion from assertion sources 101-1 through 101-n and produces attribute-associated signals based on the input ontology. According to an embodiment, the signals may comprise tagged data that associates data from the assertion sources 101-1 through 101-n with a particular attribute of the ontology 120. According to some embodiments, the attribute may be inferred from the associated assertion source. Components of the SGAM 110 need not be aggregated into one device, and may be implemented at various locations throughout the system 100 such as at the location of each assertion source 101-1-101-n. The signals and additional information produced by the SGAM 110 are stored in temporal signal store 130.

The output analysis and results system (OARS) 150 communicates with at least one of the SGAM 110 and the temporal signal store 130 to produce information based on the input ontology and assertions. As described in more detail below, the output of OARS 150 may be provided to a user via a user interface. For example, OARS 150 may output data-driven attribute values, or recommendations based on attribute values. OARS 150 may apply synthesis rules to develop new assertions from the assertions received by the system 100.

Figure 1B:
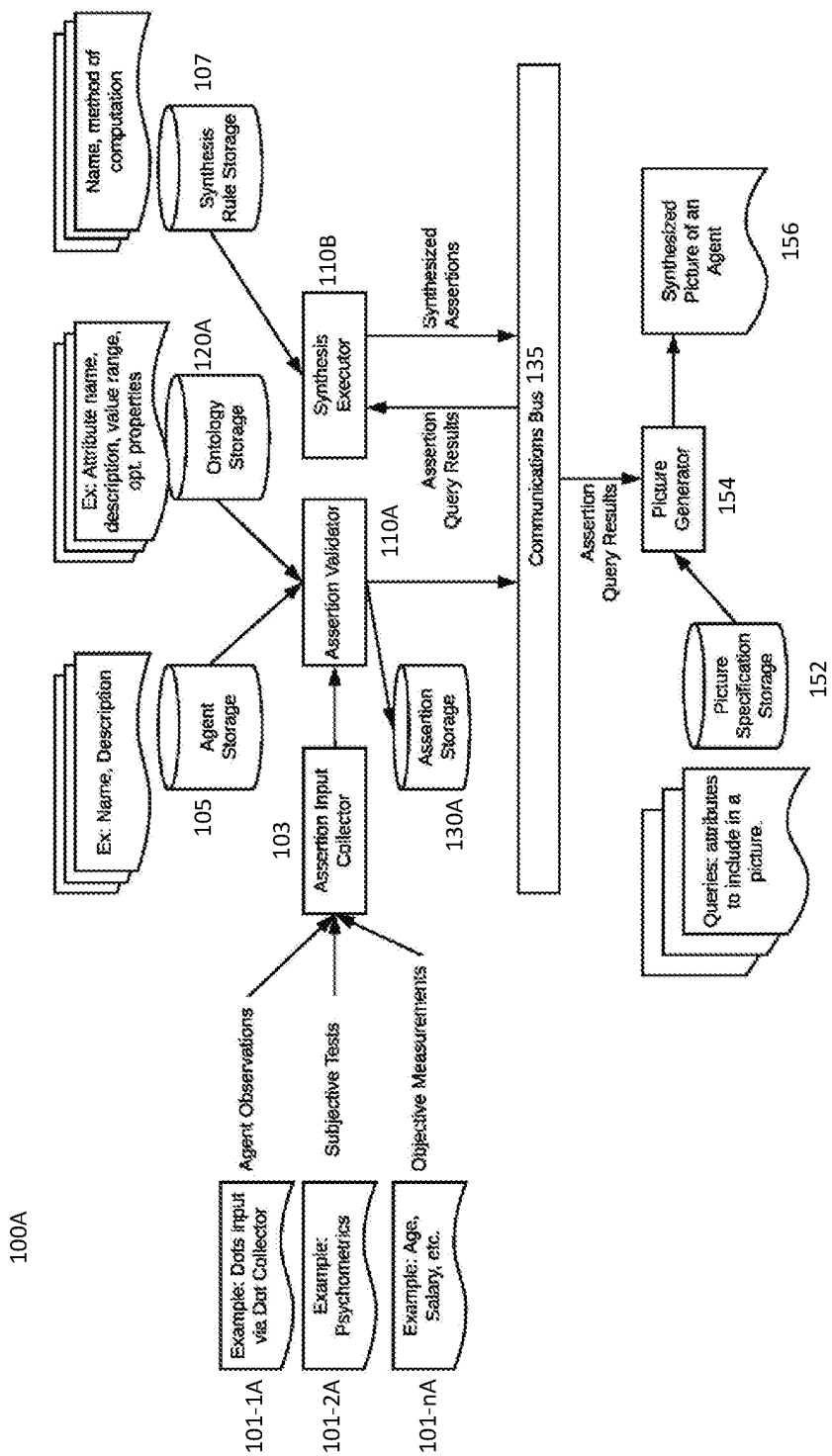

FIG. 1B illustrates an exemplary system 100A, which may be an implementation of the system 100 of FIG. 1A, according to some embodiments. As shown in FIG. 1B, the system 100 receives assertions via assertion sources 101-1A to 101-nA. For example, assertion source 101-1A receives dots, which are direct assertions about an attribute value received from a source agent about a subject agent. Other assertion sources may include psychometric test data from assertion source 101-2A or demographic data such as age and salary via assertion source 101-nA. Assertions received from assertion source 101-2A may be subjective tests or measurements whereas assertions from assertion source 101-nA may be objective measurements.

Assertions from assertion sources 101-1A to 101-nA may be provided to assertion input collector ("AIC") 103. AIC 103 may take the form of an API, for example, that receives the assertions from assertion sources 101-1A to 101-nA and serializes them onto a bus for processing, validation, and storage.

The output from AIC 103 is provided to the assertion validator 110A. Assertion validator 110A also receives information from agent storage 105 and ontology storage 120A. The ontology storage 120A stores the ontology discussed above. For example, it may include attribute names, descriptions, value ranges, and optionally properties. Agent storage 105 includes names and optionally descriptions for agents about which assertions may be made. Assertion validator 110A receives information about at least one agent from agent storage 105, at least part of the ontology from ontology storage 120A, and performs validation on the assertions received from assertion sources 101-1A to 101-nA. Validation may involve confirming that the assertion has been made about a subject agent for which the system can collect data and that the assertion is associated with at least one attribute about which the system can collect assertions. According to some embodiments, the assertion may also be associated with a source agent that made the assertion, and validation may confirm that the source agent is one from and/or about which the system can collect assertions. According to some embodiments, validation may include confirming that the assertion relates to a recognized attribute in the ontology, that the value is appropriate for the associated attribute, and that the agent and/or source are known to the system. Assertion validator 110A stores valid assertions in assertion storage 130A. Assertion storage 130A may store the assertions in the form of as numeric/binary values associated with an attribute and a subject agent. The assertion storage 130A may further store additional assertion information with each assertion, such as, but not limited to an indicator of the source (such as a source agent), the raw assertion (such as text, etc.), a weighting score based on the source, and/or other information relevant to assertions.

Assertion validator 110A can provide assertions with or without additional assertion information to communications bus 135. Communications bus 135 makes assertion data stored in assertion storage 130A available to other parts of the system. For example, synthesis executor 110B may query the assertion validator 110A via the communications bus 135 for assertion results, such as new assertions. The synthesis executor 110B may receive synthesis rules from synthesis rules storage 107, which stores synthesis rules based on names (or identifiers) and associated methods of computation, and then apply synthesis rule to the received assertions. The results of this application are synthesized assertions which are provided back over the communications bus 135 to the assertion validator 110A, which may then cause the synthesized assertions to be stored in assertion storage 130A after validation. Accordingly, the reception of assertions from assertion sources 101-1A to 101-nA may trigger the creation of new assertions. Various examples are discussed in more detail below.

Assertions may also be queried by various output analysis and results systems, such as the picture generator 154 as shown in FIG. 1B. Picture generator may receive picture information from picture specifications storage 152. Picture specification storage 152 may define particular attributes and/or rules for displaying a picture. For example, the picture specification storage 152 may store rules that require the most significant attribute or attributes associated with an agent to be displayed. Significant attributes may be defined by a system operator, and may include but are not limited to attributes with the highest or lowest scores, attributes with values that vary with statistical significance from average attribute values possessed by a population, attributes that are most important for a particular organization or user that is implementing the system 100A, etc. Other rules for identifying significant attributes are contemplated. The picture generator 154 queries assertions via the communications bus 135 based on the picture specifications received from the picture specification storage 152 and outputs a synthesized picture of an agent 156.

According to some embodiments, the picture generator 154 may include natural language generation (NLG). For example, the meta model may allow for specification in the ontology of various grammatical elements for particular attributes, such as definitions, adjective forms, noun forms, past tense verb forms, etc. In an example, attributes in an ontology may include "conceptual" and "creative." Both may belong to a category of thinking attributes. A conceptual thinker may be defined with narrative phrase "a conceptual person thinks in terms of abstractions and generalizations" whereas a creative thinker may be defined with the narrative phrase "a creative person thinks outside of the box to invent new solutions." The conceptual attribute may be associated with an adjective form of "conceptual," a noun form of "conceptual thinker," and a past tense verb form of "thought conceptually." Similarly, the creative attribute may be associated with an adjective form of "creative," a noun form of "creative person," and a past tense verb form of "was creative." A person having ordinary skill in the art would understand, based on the present disclosure, that these can be stored as components of the ontology storage 120A or as parts of the picture specification storage 152.

According to some embodiments, the picture generator 154 may be configured to produce a synthesized picture 156 including NLG based on various assertions received by the system 100A. For example, when a set of positive assertions are received about an agent relating to the "conceptual" attribute, the picture generator 154 can look up the specified grammatical elements for "conceptual" (e.g., past tense verb form "thought conceptually") to produce the statement "people noticed you thought conceptually." Where the assertions are tied to a particular event, such as a meeting, the picture generator 154 can add this context to the statement, for example, by producing the statement "people noticed you thought conceptually in this meeting." According to some embodiments, the picture generator 154 may be configured to produce a synthesized picture 156 that is based on aggregated statistics. For example, if over a period of time assertions about a particular agent demonstrate a low likelihood that the person has the "creative" attribute, the picture generator could produce the statement "on the whole, you do not appear to be a creative person" based on these aggregated assertions and the noun form "creative person." A person of ordinary skill in the art would understand based on the present disclosure that this statement can be generated for agents with creativity scores below a particular threshold, for agents having creativity scores that are lower based on a predefined ratio than other attributes, or any other type of trigger. The statements can be generated automatically in response to reception of assertions and provided to the agent or they can be generated when requested by an agent at a particular time. The system can optionally append the narrative phrases to these outputs to add context to the generated statements. Accordingly, NLG can be built into the system 100A in a way that is ontology independent. When an ontology is changed or defined, the system 100A can adapt to produce NLG without requiring changes to the structure of the system 100A.

According to some embodiments, the picture generator 154 can aggregate assertions across multiple attributes to produce a picture 156 that describes combined synthesis. For example, picture specification storage 152 or the ontology storage 12A can also include combination information, such as details about agents that are both conceptual and creative. This may take the form of a narrative, such as "people who are both conceptual and creative are comfortable in a world of ideas, extending the concepts they understand to apply to new situations." When the system 100A determines that an agent is sufficiently creative and conceptual, it can produce the following pre-determined statement: "on the whole, you appear to be conceptual and a creative person. People who are both conceptual and creative are comfortable in a world of ideas, extending the concepts they understand to apply to new situations." According to some embodiments, the picture generator can access particular assertions received during an event, such as during a meeting as discussed below, to present a picture of individuals in association with the event or present a picture of the event itself.

Figure 2:
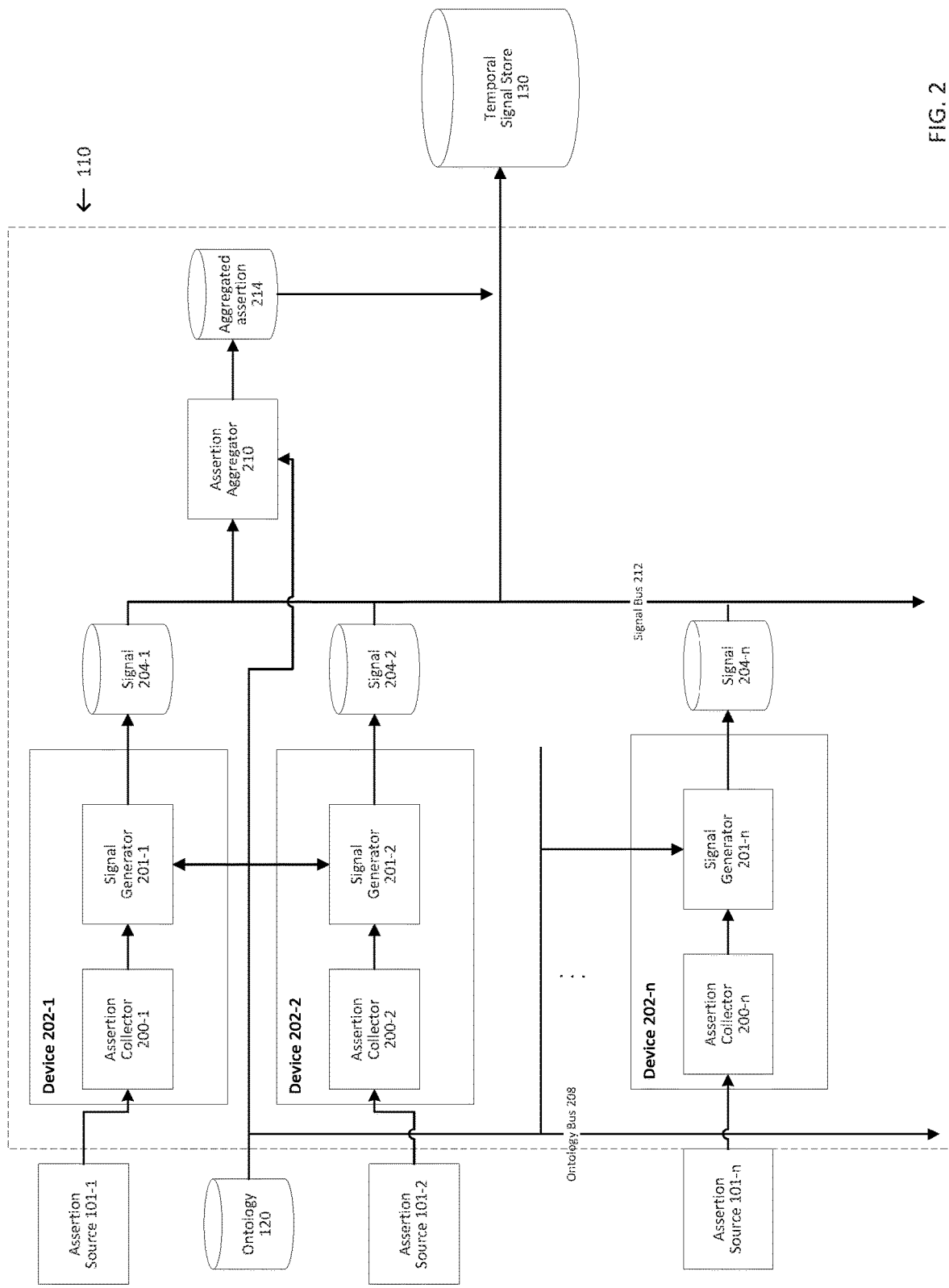
FIG. 2 illustrates an exemplary signal generators and aggregators module, according to some embodiments of the present disclosure.

FIG. 2 illustrates an exemplary SGAM 110, according to some embodiments of the present disclosure. SGAM 110 includes device 202-1 through **202-*n*, assertion collector 200-1 through 200-*n*, signal generator 201-1 through 201-*n*, signal 204-1 through 204-*n*, ontology bus 208, signal aggregator 210, signal bus 212, and signal 214. SGAM 110 communicates with assertion sources 101-1 through 101-*n*, ontology 120, and temporal signal store 130**.

As shown in FIG. 2, SGAM 110 receives assertions from assertion sources 101-1 through **101-*n*, and receives an input ontology from ontology 120 on the ontology bus 208. Ontology bus 208 allows for devices 202-1 through 202-*n* and signal aggregator 210 to access the information to access the information in ontology 120. Though not shown, a similar bus may be provided for agent information from agent storage 105** in FIG. 1B.

Devices 202-1 through **202-*n* receive assertions from assertion sources 101-1 through 101-*n* via assertions collectors 200-1 through 200-*n*, respectively. In some embodiments, assertions from each assertion source 101-1 through 101-*n* is collected by a separate assertion collector 200-1 through 200-*n*. In some embodiments, each assertions collector 200-1 through 200-*n* collects assertion from one or more assertion sources 101-1 through 101-*n*** (for example, as shown in FIG. 1B).

Synthesis rules can be applied to the output of assertion collectors 200-1 through **200-*n* by signal generators 201-1 through 201-*n*, respectively. According to some embodiments, signal generators 201-1 through 201-*n* produce signals 204-1 through 204-*n*, respectively, by combining the out of assertion collectors 200-1 through 200-*n* with ontology information, which may include signal validation as discussed above. Signal generators 201-1 through 201-*n*** may receive raw assertions from one of assertion sources 101-1 through **101-*n*, other assertions (such as those in assertion storage 130A shown in FIG. 1B), and the input ontology 120 via ontology bus 208 including properties of the attribute for which the signal will be generated. The signal generators 201-1 through 201-*n* then interpret the assertions in light of these inputs and outputs signals, such as assertions for storage in temporal store 130. For example, one of signal generators 201-1 through 201-*n* may interpret text assertions and recognize certain terms or phrases associated with a particular attribute based on the ontology 120. The signal generators 201-1 through 201-*n* may then affix one or more tags to the assertion based on the ontology 120 provided over ontology bus 208. Each of signals 204-1 through 204-*n*** is associated with at least one point of interest, such as an agent.

According to some embodiments, one or more of signal generators 201-1 through **201-*n* can be configured for natural language processing ("NLP"). For example, an assertion collector can receive audio, video, and/or text data from assertion sources. A signal generator can parse the audio, video, and/or text data to produce a stream of data, such as a text stream, that can be processed for synthesizing assertions. This can involve applying one or more text recognition, voice recognition, and/or lip-reading algorithms to produce the stream of data. The stream of data can then be parsed for assertions relating to attributes. For example, a stream of data comprising the text "John Doe, that was smart" can be parsed to be an assertion about an intelligence attribute based on the word "smart," and more particularly an assertion that the subject has high intelligence based on the phrase "was smart." Synthesis rules can be stored, for example as an ontology 120A or in synthesis rule storage 107** and provided to signal generators in order to parse the stream of data.

Natural language processing can be implemented using a one or more of a variety of different techniques. According to some embodiments, the stream of data can include meta data, such as information about a source agent and a subject agent of the same type. The meta data can be compiled from a number of different types of information, such as, but not limited to, the assertion source (e.g., a microphone or email address associated with a particular agent) to identify the source agent; voice or image recognition to identify the source agent; voice, video, and/or voice recognition algorithms to identify the subject or source agents (e.g., identifying "John Doe" from the data stream "John Doe, that was smart" or identifying the source of Jane Doe based on facial recognition to identify Jane Doe as the one who spoke the phrase "John Doe, that was smart"); contextual clues (e.g., information about proximity of a particular agent to the assertion source based on technologies such as GPS, for example showing that John P. Doe was in the location where the assertion was received whereas John L. Doe was at a different location to identify the subject agent as John P. Doe) to identify a source or subject agent; or any other method of obtaining information about the source and/or subject agents.

According to some embodiments, the system only identifies or receives meta data about the subject agent. In such situations, the assertion can be stored without a source agent. According to an alternative embodiment, the assertion can be stored with a situational source, such as a particular meeting, without association with a particular source agent. Assertions from such situational sources can be evaluated similarly to assertions from source agents. For example, synthesis rules can produce believability weights for such assertions based on available information, such as the typical believability of assertions from meetings relative to other assertions, or the aggregate believability of all of those agents present at the meeting. According to some embodiments, the assertions are not associated with subject or source agents. For example, such assertions can be associated with an event (e.g., the meeting was tense).

The signals 204-1 through **204-*n* are then provided along signal bus 212 to the assertion aggregator 210 and temporal signal store 130. The assertion aggregator 210 compiles the signals provided on signal bus 212 and performs certain functions such as weighting the value of assertions (e.g., for lower weight for a large number of assertions received based on a same event or scaling assertions from a particular source based on how that source rates other agents, e.g., normalizing for harsh or easy evaluators) and/or add decay information that may cause the relative weight of an assertion decay over time based on things like the ontology and information about the agent. Assertion aggregator 210 then provides the aggregated assertion 214 to the temporal signal store 130 based on the aggregated signals. Temporal signal store 130 stores the signals 204-1 through 204-*n* and the aggregated assertion 214 from signal aggregator 210. According to an embodiment, the temporal signal store 130 also includes timing information or event information (e.g., associated with a period of time such as a meeting or presentation) for when the signals were generated. In some embodiments, each signal is associated with a timestamp indicating when the signal was generated or updated. The temporal signal store 130 may organize information based on attributes, timing, assertion sources, and/or points of interest. According to an embodiment, temporal signal store 130 is a database that provides for easy access to signals based on attributes, timing, assertion sources, and/or points of interest. Such access is described, for example, with respect to FIGS. 4-6. Temporal signal store may contain weighting data for each of the signals, and may also be updated based on a change in the input ontology 120**.

According to an embodiment, the SGAM 110 may be implemented based on an input ontology 120 constructed to determine characteristics about employees at an organization. Points of interest can be people, and attributes may be implemented to determine relevant individual characteristics, such as, but not limited to values, abilities, skills, personality, strengths, and/or weaknesses. For example, an attribute can be creativity. One of assertion collectors 200-1 through **200-*n* can collect assertions from an assertion source 101-1 through 101-*n*, such as polls asking employees to rate the creativity of others. The ratings may be relative to other employees, such as a ranking from first to last or best to worst, or based on an arbitrary scale, such as 1-10. One of signal generators 201-1 through 201-*n* may associate a tag for creativity and/or other attributes with the assertions received from the survey, and produce a signal to the temporal signal store 130 and the signal aggregator 210. According to an example, the input ontology 120 may specify that creativity attribute is a "takes-one-to-know-one" attribute, and thus may weight more heavily the creativity ratings from employees that possess higher creativity ratings. Accordingly, signal aggregator 210 may weight signals based on the creativity value in temporal signal store 130 for the employee providing the rating. This weighted signal is then provided to the temporal signal store 130**. According to an embodiment, attribute values may be updated whenever new assertions are collected. This may involve readjusting the weighting of signals in the temporal signal store.

Figure 3:
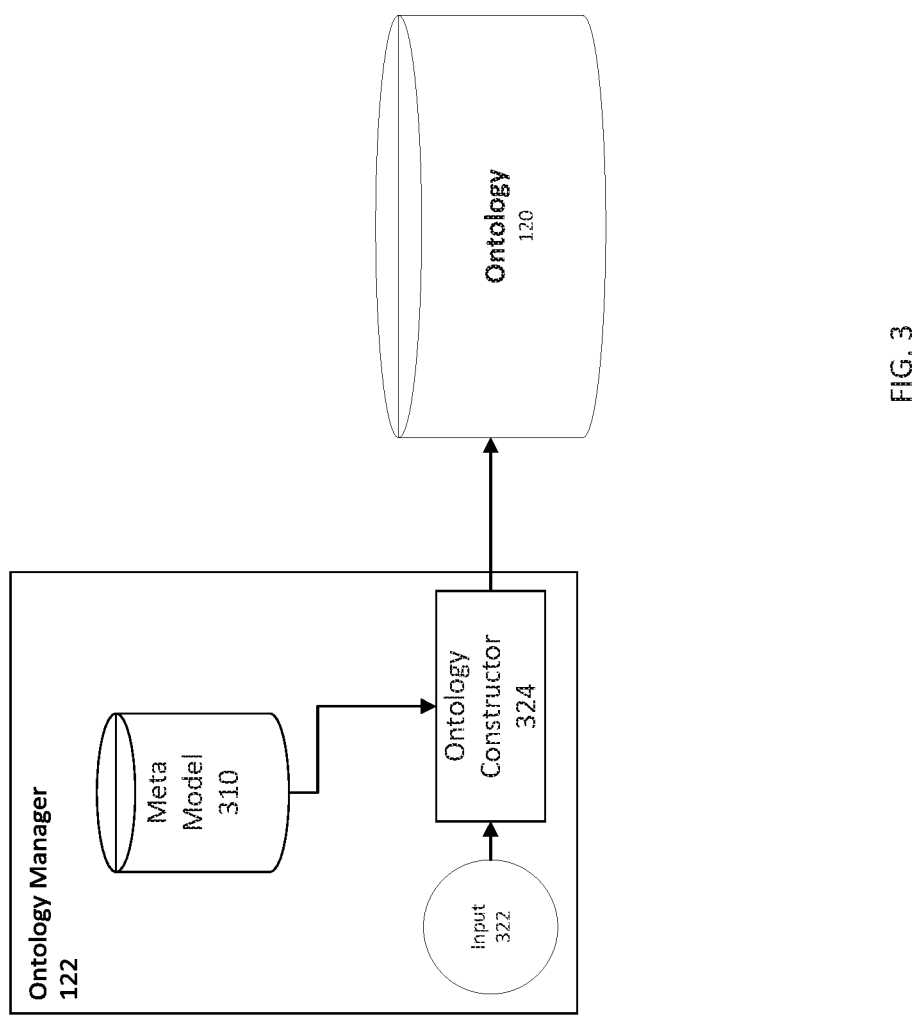
FIG. 3 illustrates an ontology manager, according to some embodiments of the present disclosure.

FIG. 3 illustrates an ontology manager 122, according to some embodiments of the present disclosure. The ontology manager 122 includes a meta model 310, a user interface (UI) 322, and an ontology constructor 324. Ontology manager 122 outputs ontology 120.

Ontology manager 122 is configured to specify an ontology based on a meta model 310. The meta model 310 allows for specification of attributes, attribute categories, and attribute properties. Ontology constructor 324 includes the meta model 310 as a structure in which an ontology may be specified. Ontology constructor 324 also receives an input via a UI 322, for example from a user or system operator, that specifies particular attributes, attribute categories, and attribute properties using the language of the ontology. According to an embodiment, the UI 322 of the ontology manager 122 includes a graphical user interface (GUI) that prompts users to input attributes, attribute categories, and attribute properties.

As described above, the meta model 310 specifies how the system defines and handles attributes in general: attribute properties, attribute categories, attribute derivations, values, confidences, multiple value sources etc. In some embodiments, the meta model is preconfigured and can be used to specify application-specific ontologies. The ontology is the "language" used to specialize the meta model to a particular purpose. The precise attributes and relationships, which constitute an ontology, are configurable. For example, attributes can be added, related, etc.

According to an embodiment, the ontology manager 122 may be used to make changes to an existing ontology 120. For example, if an ontology contains attributes called "Common Sense" and "Practical," and a system operator decided to remove those attributes in favor of a different attribute called "Pragmatic," the ontology manager 122 would determine what would be done with the old data. The ontology manager 122 might help update the ontology 120 and then administer changes to the rest of the system based on the updates.

As described above, the ontology 120 is the collection of attributes or features used to describe what points of interest are like and what is required for of those points of interest. For example, for a system designed for employees or members of an organization, points of interest may be employees, and the ontology 120 may describe characteristics relevant to employees that relate to job performance or how they approach their job. The ontology 120 may include categories of those attributes and relations between them. For example, attribute categories may include: Cognitive, Interpersonal, Internal. Cognitive attributes may include things like Conceptual, Logical, Analytical, etc. The ontology 120 conforms to the meta model 310. The ontology 120 may be configured either in part or entirely to meet the needs of a given system operator.

Figure 4:
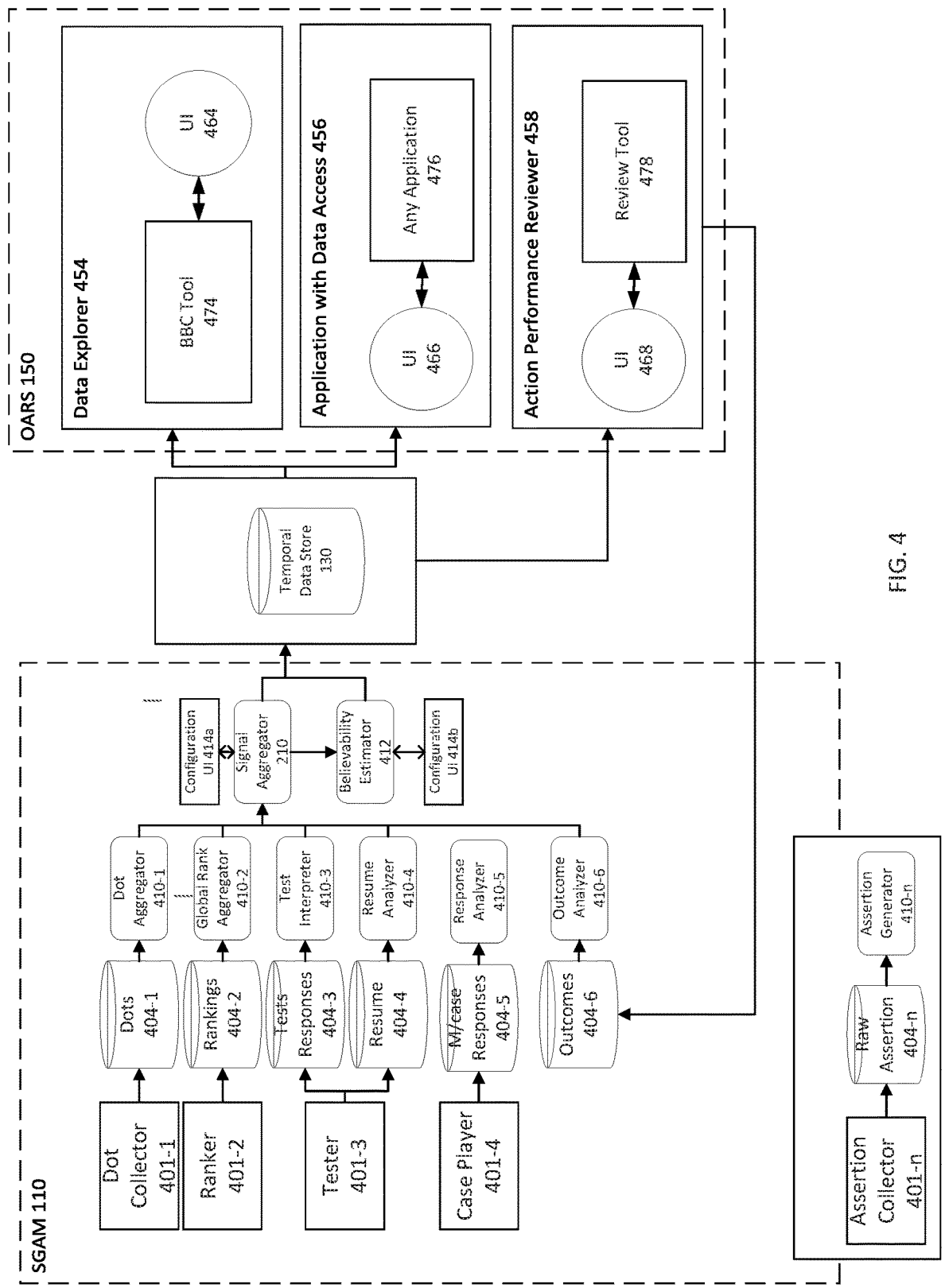
FIG. 4 illustrates an exemplary signal generators and aggregators module and an exemplary output analysis and results system, according to some embodiments of the present disclosure.

FIG. 4 illustrates an exemplary SGAM 110 configured to receive input assertions from a variety of different assertion sources, and exemplary OARS 150, according to some embodiments of the present disclosure. Like the SGAM 110 of FIG. 2, the SGAM 110 may include (or interface with) various assertion sources and signal generators. In particular, SGAM 110 may include assertion sources including dot collector 401-1, ranker 401-2, and tester 401-3 that provide assertions, such as dots 404-1, rankings 404-2, test responses 404-3, resume 404-4, and M/case responses 404-5 to signal generators such as dot aggregator 410-1, global rank aggregator 410-2, test interpreter 410-3, resume analyzer 410-4, and response analyzer 410-5, for application of synthesis rules. SGAM 110 further receives outcomes 404-6 as input from OARS 150, and provides outcomes 404-6 to outcome analyzer 410-6. SGAM 110 further includes configuration UIs 414a, 414b, signal aggregator 210, and believability estimator 412. OARS 150 may include an assertion explorer 454 having a BBC tool 474 and a UI 464, an application with data access 456 having a UI 466 and any application 476, and an action performance reviewer 458 having a UI 468 and review tool 478.

The SGAM 110 of FIG. 4 is designed to receive assertions about points of interest from different assertion sources via dot collector 401-1, ranker 401-2, and tester 401-3. According to an example, dot collector 401-1 receives responses from assertion sources that directly output assertions about a point of interest. For example, a dot may be a rating from 1 to 10 of a point of interest offered by an employee or a member of an organization. The dot may directly relate to an attribute. For example, a dot may be a rating of 7 out of 10 for a "creativity" attribute received from one employee (assertion source) about another employee (point of interest). Each rating or "dot" 404-1 is aggregated by dot aggregator 410-1 as discussed above for purposes of weighting, etc.

According to another example, SGAM 110 receives rankings 404-2 from ranker 401-2. Rankings may be similar to dots, but are relative to other points of interest. For example, a ranking may be an ordered set of points of interest ranked based on a specified attribute. For an SGAM 110 configured to receive information about employees or members of an organization, the rankings 404-2 may be a ranking received from one employee (assertion source) of a number of other employees (points of interest) based on an attribute, such as creativity. Global rank aggregator 410-2 aggregates rankings about multiple points of interest from multiple assertion sources.

According to another example, SGAM 110 receives test results via tester 401-3. According to an embodiment, test results may include test responses 404-3, such as text responses offered by human points of interest in response to test questions. For example, the tester 401-3 may collect text responses to open ended behavioral questions asking employees how they would respond to a hypothetical situation. For any given attribute, test questions may be designed or selected that "read" on that attribute. Test interpreter 410-3 receives the test responses 404-3 and applies the input ontology 120 in order to determine information about attributes of the point of interest. For example, the system operator may construct a function that transforms the responses 404-3 to questions on the tester 401-3 into an estimate of values for a given attribute. According to an embodiment, test interpreter 410-3 may use terms associated with certain attributes based on an ontology and produce corresponding signals. According to another embodiment, test interpreter 410-3 may use a weighted average of all responses from different points of interest. According to another example, the tester 401-3 receives text file that is not responsive to test questions, such as a resume 404-4. The resume analyzer 410-4 analyzes the text similarly to test interpreter 410-3 and outputs a signal based on the text-based or written assertions.

According to an embodiment, the SGAM 110 may be expanded by adding a new device 402-n. The new device 402-n is configured with an assertion collector 401-n to collect a particular type of assertions, such as, but not limited to ratings, rankings, text files, images, videos, audio, outcomes, results, or other formats of assertions. The raw assertion 404-n is fed to the assertion generator 410-n that applies the ontology 120 to output an assertion from the raw assertion 404-*n*. Accordingly, any number of devices may be added in order to obtain more information or different types of information about points of interest.

The outputs from dot aggregator 410-1, global rank aggregator 410-2, test interpreter 410-3, resume analyzer 410-4, and response analyzer 410-5 are aggregated by signal aggregator 210. According to some embodiments, signal aggregator 210 applies synthesis rules received from configuration UI 414. Signal aggregator 210 may weight signals based on aggregated information about prior assertions as discussed above and derive attribute values for particular points of interest based on each different type of signal. Accordingly, attribute values may change over time as more assertions are collected about any given point of interest.

The signals from dot aggregator 410-1, global rank aggregator 410-2, test interpreter 410-3, resume analyzer 410-4, and response analyzer 410-5 may also be provided to believability estimator 412 to provide weighting info to the signals. For example, as discussed above, a creativity attribute may possess the "takes-one-to-know-one" property. If the signal is a dot collected by a first agent (assertion source) about a second agent (point of interest), the dot would be weighted based on the creativity score of the first agent. The existence of properties relating to believability can be set forth in the meta model and specified in particular ontologies. Accordingly, changes to the ontology does not require changes to the way believability is calculated. Thus, the system can flexibly accommodate changes to ontologies while continuing to provide assertions and weightings about believability. According to some embodiments, a threshold attribute value may be required from a source agent before influencing the attribute value of a subject agent. According to another example, for a signal from the resume analyzer, the believability estimator 412 may provide more weight to the signal relating to an attribute value with a believability score based on how well the resume analyzer measures that particular attribute. This believability score may be derived from aggregated data comparing various assertion sources or may be input by a system operator. According to an embodiment, aggregated data from various assertion sources may be weighted based on outcomes. According to an embodiment, the believability scores are also provided with time-variant indicators that indicate that believability is to vary with time. For example, a resume may be the most accurate gauge available of an employee's characteristics on their first day of work, but may decrease in believability as more information is collected, and as the employee learns more on the job. Accordingly, the indicator may cause the weighting to decrease over time or as more data is gathered. The aggregated signals and believability scores are provided to temporal signal store 130.

As shown in FIG. 4, OARS 150 may include a variety of subsystems, such as data explorer 454, application 456, and action performance reviewer 458, according to an embodiment. OARS 150 communicates with the temporal signal store to access signals produced and aggregated by the SGAM 110. As in other embodiments of the present disclosure, each subsystem need not be included on the same device or machine and may be considered separate systems.

According to an embodiment, OARS 150 may include a data explorer 454 for exploring assertions about individuals. Data explorer 454 has a UI 464 and a "Baseball Card" ("BBC") tool 474. The UI may take a variety of forms for displaying assertions/assertion information, such as a computer terminal with a keyboard and a mouse for input and a display, a tablet, or a smart device. Data explorer 454 has access to the signals in temporal signal store, including relevant tags and analysis produced by SGAM 110. In operation, BBC tool 474 aggregates information in temporal signal store 130 by particular points of interest to create a "baseball card" for each point of interest. Upon input from the UI 464 to the BBC tool 474, attribute data for a particular point of interest, or for a set of points of interest may be retrieved from the temporal signal store 130. According to an embodiment, the data explorer 454 displays this information at the UI 464. The information displayed may be the synthesized picture of an agent 156 as discussed with reference to FIG. 1B. According to some embodiments, a user may be able to sort through the assertions in the temporal data store by filtering by agent, attribute, attribute category, time period, or any other relevant information.

According to some embodiments, an application with data access 456 can include a tracker tool configured to track interactions between participants, such as at a meeting. In this tool, meeting participants create assertions about each other according to the attributes of the ontology. Synthesis rules are used to generate new assertions based on these assertions, which can include, for example, weighted averages or other higher-level assertions about people or how they interact with one another in the context of the meeting. According to some embodiments, the tracker tool can be associated with a particular event, such as a meeting. In an example, the tracker tool can compare assertions received during the meeting to determine whether people agree or disagree with one another about a participant's performance in the meeting. According to another example, the tracker tool can connect with tester 401-3 or case player 401-4 to ask questions of the participants, including multiple choice, true or false, or ranking questions. Assertions from these survey questions, such as summary statistics and agreement determinations can be generated from these questions.

By retrieving the assertions made by the participants during the meeting, the system, the picture of the participants and interactions can be summarized using natural language generation as discussed above as well as tabular and graphical renderings. This not only summarizes the interactions among participants, highlighting and summarizing how participants responded to questions, but also provide a textual summary via natural language generation of the assertions that transpired.

FIG. 5 is a flow chart showing a process for aggregating and generating new assertions, according to some embodiments of the present disclosure. At step 502, the computerized method begins by storing agent analysis data. This agent analysis data can include agent indicators, attributes, synthesis rules, and output agent associations. As discussed in more detail throughout the present disclosure, the attributes may be configurable based on a specified ontology (e.g., as described with reference to FIG. 3), and the synthesis rules may be used to process assertions made about an agent and produce new assertions therefrom. Accordingly, the synthesis rules may specify one or more associated input attributes, one or more associated output attributes, one or more computational operations to perform on an attribute-specific value, and one or more output agent associations, according to some embodiments.

The specification of input attributes may indicate which attribute or attributes may be used in the application of the synthesis rule. These input attributes may serve a variety of functions during application of the synthesis rule. According to some embodiments, an input attribute may be specified to trigger the application of the synthesis rule. For example, where the input attribute is a sub-attribute of another attribute, the input attribute may be the sub-attribute, and it may be used to trigger the creation of an assertion about the other attribute. In such an example, if "verbal communication skills" is a sub-attribute of "interpersonal skills," the synthesis rule may be applied when the input attribute is "verbal communication skills." The output attribute in this case may be specified as "interpersonal skills." The computational operation may thus receive an assertion about "verbal communications skills" and output an assertion about "interpersonal skills." The output attribute-specific value for "interpersonal skills" may include weighting based on a number of factors, such as the existing average (or weighted/time adjusted average) of the subject agent's "verbal communications" and/or "interpersonal skills" attributes, the existing average (or weighted/time adjusted average) of the source agent's "verbal communications" and/or "interpersonal skills" attributes (e.g., for a takes-one-to-know-one attribute), or based on other factors indicating believability or weight, such as those based on the context or timing of the assertion (e.g., during an annual review vs. in relation to an unimportant project) or based on the agents themselves.

An input attribute may also or alternatively indicate an input attribute value used in the application of the synthesis rule. In such cases, a value associated with the input attribute for one of the source or subject agents is used in the application of the computational operation or to determine if the computational operation should be applied. For example, as discussed above, the synthesis rule may involve weighting or thresholding based on another attribute different from the one associated with an input assertion. In such cases, the synthesis rule may instruct the system to query attribute values for the other attribute (of either the source or subject of the received assertion) in order to apply the specified computational operations.

The specified output attribute indicates the to which attribute the attribute-specific value resulting from the computational operations will be associated. Multiple output attribute indicators may be provided with multiple computational operations such that the input attribute or attributes trigger a number of different output attribute values to be generated and stored as assertions.

As discussed above, the attribute-specific value output based on the synthesis rule may be stored in association with an agent. Accordingly, for an assertion received from a source agent about a subject agent, the synthesis rule may specify an output agent association for one or more of the output attributes such that the attribute-specific value(s) output based on the synthesis rule are stored in association with the appropriate one of the source and/or subject agent. For example, where a synthesis rule receives an assertion from a source agent that has a low attribute-specific value, a synthesis rule may specify "harshness" as an output attribute, and may accordingly store an attribute-specific value for "harshness" determined from a computational operation on the assertion's low attribute-specific value in association with the source agent, even though the received assertion related to the subject agent.

At step 504, an assertion may be received. The assertion may include identifications of source and subject agents, an attribute, and an attribute-specific value. According to some embodiments, the assertion may be a dot including a numerical rating for an identified attribute of the subject agent by the source agent as discussed in more detail above. More complex assertions are contemplated. For example, the system may receive text and extract an assertion therefrom. This may involve processing aspects of the text such as metadata to identify the author (i.e., source) and subject. Furthermore, the text may be interpreted to identify at least one of the source agent, subject agent, attribute, and/or attribute-specific value. For example, if person X sends an email to person Y that includes the text "I thought you did a good job presenting today," the system may interpret the email to indicate that the source is person X, the subject is person Y, that "presenting" implies a "verbal communication" attribute, and that "good job" indicates an above average score. The synthesis rule may translate the above average score into an attribute specific value, for example based on a preset definition of the phrase "good job" and/or based on a comparison with prior assertions about either person X, person Y, and/or other agents in the system (e.g., normalization).

At step 506, the synthesis rule may be applied by performing computational operation of the synthesis rule to produce the output attribute-specific value. According to some embodiments, the application of the synthesis rule may involve creating new assertions based on the input attribute-specific value. As discussed above, this may be based on at least one input attribute-specific value. For example, if the computational operation is a thresholding or weighting function based on things including, but not limited to, an attribute specific value of the source or subject of the assertion for the attribute of the input attribute-specific value or another attribute, the computational operation may be performed to adjust the input attribute-specific value to produce the output attribute specific value. As discussed above, this may additionally or alternatively be based on the input attribute. For example, the synthesis rule may produce an output attribute-specific value based on the input attribute-specific value to be stored with a different attribute as discussed above with reference to attribute and sub-attributes. According to some embodiments, such as for takes-one-to-know-one attributes, the synthesis rule may be applied based on the input attribute. According to this example, the output attribute-specific value may be unchanged from the input attribute-specific value, but may be associated with a weighting factor that increases or decreases the relevance of the output attribute-specific value.

At step 508, the output attribute-specific value may be stored in association with the source or subject agent based on the one or more output agent associations. At step 510, a source or subject agent profile is generated based on the output attribute-specific value. The source or subject agent profile may also be generated based on a number of different other previously received or processed assertions, for example as discussed in more detail above with reference to FIG. 4

According to some embodiments, the attribute-specific value received in the assertion signal is first stored and then updated based on the synthesis rule. For example, the output attribute-specific value may be a weighting factor, or an adjustment stored with or that changes the stored attribute specific value. According to some embodiments, the output attribute-specific value comprises weighting factor or an adjustment stored with or that changes another attribute specific value stored prior to reception of the assertion.

According to some embodiments, as discussed above, the system may receive a plurality of assertions and store them along with output attribute-specific values in the temporal signal store 130 of FIGS. 1A and 2 or the assertion storage 130A of FIG. 1B. This may allow for other attribute-specific values to be retrieved and used in the application of synthesis rules as described above with reference to FIG. 5.

According to some embodiments, the synthesis rules discussed throughout the present disclosure may be static.

However, according to some additional embodiments, some or all of the synthesis rules may be adjusted automatically or manually so as to reflect information learned from the input assertions. For example, correlations may be identified between attribute values of particular attributes, and synthesis rules may be updated or created to reflect those correlation. Thus, when an assertion is received for an agent about one attribute, a correlated other attribute may also be updated for the agent. Furthermore, agents may be ranked based on certain attribute values. For example, the system may apply population statistics that indicate an agent's percentile above or below the mean, median, mode, etc. for particular attributes or sets of attributes. Additional synthesis rules may be triggered based on these population statistics and may include, for example, weighting assertions about or by the agent about which the population statistics were generated.

According to some embodiments, for example as discussed with reference to FIG. 4, additional assertions may be input into the system that were not generated by agents. For example, personality test or other questionnaires may be provided to agents, and their response may be input into the system as additional assertions. These may be used to generate agent profiles, and may also be used to generate population statistics across the set of agents where there are few agent-generated assertions or where such assertions are considered unreliable.

According to some embodiments, synthesis rules are triggered based on the input of new assertions. According to some alternative embodiments, synthesis rules may be run in a "batch mode" at a scheduled interval or when a specified threshold number of assertions have been received.

The methods and systems described above constitute an improvement computing systems and methods. For example, according to some embodiments, the methods and systems described above provide a system architecture that allows agents to provide assertions about other agents that then outputs additional assertions. The systems and methods are flexible and support customizable ontologies for a variety of implementations. By structuring systems and methods in the ways described in the present application, real time updates may be made to the picture of an agent that can influence the picture of other agents.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. A computerized method for creating agent profiles, the method comprising:
   storing, by a computing device, agent analysis data in a data store, the agent analysis data including:
      a plurality of agent indicators, each of which uniquely identify a person,
      a plurality of attributes, and
      a plurality of synthesis rules, each synthesis rule specifying:
         at least one associated input attribute of the plurality of attributes,
         at least one associated output attribute of the plurality of attributes,
         at least one computational operation to perform on an attribute-specific value associated with the at least one associated input attribute, the computational operation yielding at least one output attribute-specific value for at least one of the at least one associated output attribute, and
         an output agent association, the output agent association indicating an assignment of the output attribute-specific value to one of a source agent and a subject agent;
   receiving, by the computing device, an assertion signal from at least one source agent, the assertion signal comprising:
      an identification of a source agent indicator from the plurality of agent indicators,
      an identification of a subject agent indicator from the plurality of agent indicators,
      an identification of a first attribute from the plurality of attributes, and
      an identification of a first attribute-specific value;
   applying a synthesis rule of the plurality of synthesis rules based on at least one of:
      the identification of the source agent indicator,
      the identification of the subject agent indicator,
      the identification of the first attribute, and
      the identification of the first attribute specific value,
      wherein applying the synthesis rule includes performing the at least one computational operation associated with the synthesis rule to yield the at least one output attribute-specific value;
   storing the at least one output attribute-specific value in association with at least one of the source agent and the subject agent based on the output agent association of the at least one synthesis rule; and
   generating at least one of a source agent profile and a subject agent profile based on the stored at least one output attribute-specific value.

2. The computerized method of claim 1, wherein the plurality of attributes are configurable based on a specified ontology.

3. The computerized method of claim 1, wherein the performing the at least one computational operation is based on one of the identification of the source agent indicator and the identification of the subject agent indicator, and wherein the performing the at least one computational operation comprises retrieving at least one of:
   at least one first stored attribute-specific value for the first attribute stored in association with the one of the identification of the source agent indicator and the identification of the subject agent indicator; and
   at least one second stored attribute-specific value for a second attribute different from the first attribute stored in association with the one of the identification of the source agent indicator and the identification of the subject agent indicator.

4. The computerized method of claim 3, wherein the computational operation further comprises at least one of:
   comparing the at least one first stored attribute-specific value or the at least one second stored attribute-specific value to a threshold; and
   comparing at least one first stored attribute-specific value or the at least one second stored attribute-specific value to the first attribute-specific value from the assertion signal.

5. The computerized method of claim 1, wherein the computational operation comprises at least one of:
   averaging attribute values associated with the subject agent indicator;
   filtering attribute values associated with the subject agent indicator based on a threshold;
   weighting attribute values associated with the subject agent based on stored information associated with at least one of the subject agent indicator and the source agent indicator;
   computing an update to the stored first attribute-specific value associated with at least one of the source agent indicator and the subject agent indicator;
   computing an update to the stored second attribute-specific value associated with at least one of the source agent indicator and the subject agent indicator.

6. The computerized method of claim 5, wherein the stored information comprises a believability score associated with at least one of the subject agent indicator and the source agent indicator.

7. The computerized method of claim 1, wherein the generating at least one of a source agent profile and a subject agent profile based on the output attribute-specific value comprises generating text summarizing at least the output attribute-specific value and at least one other assertion.

8. The computerized method of claim 1, wherein at least one of the plurality of attributes comprises an observable attribute of at least one of a person's personality or cognitive style.

9. The computerized method of claim 1, wherein the receiving, by the computing device, an assertion signal from the at least one source agent comprises receiving a plurality of assertion signals to yield a plurality of output attribute-specific values for at least one subject agent.

10. The computerized method of claim 9, further comprising adjusting at least one of the plurality of output attribute-specific values based on others of the plurality of output attribute-specific values.

11. The computerized method of claim 10, wherein the adjusting the at least one of the plurality of output attribute-specific values comprises normalizing the plurality of output attribute-specific values to an expected or desired distribution.

12. The computerized method of claim 9, further comprising:
comparing at least one of the plurality of output attribute-specific values associated with one subject agent and one attribute with at least one of a threshold and others of the plurality of output attribute-specific values associated with the one attribute; and
identifying if the at least one of the plurality of output attribute-specific values is an outlier.

13. The computerized method of claim 9, further comprising ranking at least two subject agents based on output attribute-specific values associated with the at least two subject agents for at least one attribute.

14. The computerized method of claim 13, further comprising generating a second assertion signal associated with at least one of the two subject agents based on the ranking.

15. The computerized method of claim 9, further comprising generating a graphical user interface to provide a user with access to at least a subset of the plurality of output attribute-specific values, wherein the graphical user interface includes:
at least one selection input configured to select output attribute-specific values based on at least one of an agent indicator, an attribute, a specified time period, and a specified attribute-specific value range; and
a display element configured to display the at least a subset of the plurality of output attribute-specific values based on input from the at least one selection input.

16. The computerized method of claim 9, further comprising updating at least one of the synthesis rules based on the plurality of output attribute-specific values.

17. The computerized method of claim 1, wherein at least one of the identification of the first attribute from the plurality of attributes and the identification of the first attribute-specific value comprises text, audio, or video data, and wherein the computerized method further comprises processing the text, audio, or video data to determine the at least one of the first attribute and the first attribute-specific value.

18. The computerized method of claim 1, further comprising associating the assertion signal with at least one event or time.

19. The computerized method of claim 18, further comprising comparing the at least one output attribute-specific value with at least one previously generated output attribute-specific value associated with the same attribute to produce an assertion about the at least one event.

20. The computerized method of claim 1, further comprising
receiving at least one assertion from a non-agent about the subject agent, the assertion comprising:
an identification of the subject agent indicator from the plurality of agent indicators, and
an identification of the first attribute from the plurality of attributes, and
an identification of a non-agent rated first attribute-specific value;
storing the non-agent rated attribute-specific value in association with the subject agent; and generating the subject agent profile based on the stored at least one output attribute-specific value and the stored non-agent rated first attribute-specific value.

21. The computerized method of claim 1, wherein the assertion signal comprises one or more of audio, video, and text data, and wherein the identification of the first attribute from the plurality of attributes and the identification of a first attribute-specific value are extracted from the assertion signal using natural language processing.

22. The computerized method of claim 1, further comprising generating natural language based on at least one attribute-specific grammatical element and one or more of the at least one output attribute-specific value and the first attribute-specific value.

23. A system comprising:
at least one memory; and
one or more processors coupled to the at least one memory, the one or more processors being configured to read instructions from the at least one memory that, during execution, cause the one or more processors to perform operations comprising:
storing agent analysis data in a data store, the agent analysis data including:
a plurality of agent indicators, each of which uniquely identify a person,
a plurality of attributes, and
a plurality of synthesis rules, each synthesis rule specifying:
at least one associated input attribute of the plurality of attributes,
at least one associated output attribute of the plurality of attributes,
at least one computational operation to perform on an attribute-specific value associated with the at least one associated input attribute, the computational operation yielding at least one output attribute-specific value for at least one of the at least one associated output attribute, and
an output agent association, the output agent association indicating an assignment of the output attribute-specific value to one of a source agent and a subject agent;
receiving an assertion signal from at least one source agent, the assertion signal comprising:
an identification of a source agent indicator from the plurality of agent indicators,
an identification of a subject agent indicator from the plurality of agent indicators,
an identification of a first attribute from the plurality of attributes, and
an identification of a first attribute-specific value;
applying a synthesis rule of the plurality of synthesis rules based on at least one of:
the identification of the source agent indicator,
the identification of the subject agent indicator,
the identification of the first attribute, and
the identification of the first attribute specific value,
wherein applying the synthesis rule includes performing the at least one computational operation associated with the synthesis rule to yield the at least one output attribute-specific value;
storing the at least one output attribute-specific value in association with at least one of the source agent and the subject agent based on the output agent association of the at least one synthesis rule; and generating at least one of a source agent profile and a subject agent profile based on the stored at least one output attribute-specific value.

\* \* \* \* \*